United States Patent [19]

Bonnaud et al.

[11] Patent Number: 5,286,735
[45] Date of Patent: Feb. 15, 1994

[54] DERIVATIVES OF 4-AMINOMETHYLPIPERIDINE, THEIR PREPARATION AND THEIR USE AS THERAPEUTICS

[75] Inventors: Bernard Bonnaud, Lagarrigue; Dennis Bigg, Castres, both of France

[73] Assignee: Pierre Fabre Medicament, Boulogne, France

[21] Appl. No.: 944,433

[22] Filed: Sep. 14, 1992

[30] Foreign Application Priority Data

Sep. 16, 1991 [FR] France ................... 91 11382

[51] Int. Cl.$^5$ ............... A61K 31/445; C07D 405/12; C07D 409/12; C07D 411/12
[52] U.S. Cl. ............... 514/321; 514/319; 514/320; 514/324; 546/156; 546/157; 546/202; 546/205
[58] Field of Search ............ 546/196, 197, 202, 205; 514/321, 324, 319, 320

[56] References Cited

U.S. PATENT DOCUMENTS

| | | | |
|---|---|---|---|
| 4,499,100 | 2/1985 | Kluge | 546/197 |
| 5,077,288 | 12/1991 | Lavielle | 544/237 |
| 5,126,366 | 6/1992 | Stack | 546/197 |

OTHER PUBLICATIONS

Malen et al "Preparation of 2-[4-(Aminomethyl)Piperidine Benzothiazole, as Serotoninergic Agonist". CA 115, 256155b (1991).

*Primary Examiner*—C. Warren Ivy
*Assistant Examiner*—Celia Chang
*Attorney, Agent, or Firm*—Gordon W. Hueschen

[57] ABSTRACT

The application discloses pharmacologically-active derivatives of 4-aminomethyl piperidine having the general formula 1

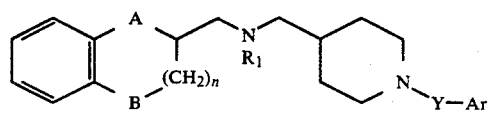

wherein the symbols have the meanings set forth in the Specification, as well as pharmaceutically-acceptable acid addition salts thereof, the use of the compounds as serotoninergic receptor ligands and for the treatment of anxiety, depression, and other related serotoninergic system disorders, pharmaceutical compositions thereof, and a method for their preparation.

6 Claims, No Drawings

DERIVATIVES OF 4-AMINOMETHYLPIPERIDINE, THEIR PREPARATION AND THEIR USE AS THERAPEUTICS

FIELD OF INVENTION

The present invention has as its object new and valuable pharmacologically-active 1-substituted-4-substituted aminomethylpiperidine compounds, a process for their preparation, pharmaceutical compositions thereof, and a method of treating therewith.

OBJECTS OF THE INVENTION

It is an object of the invention to provide novel 1-substituted-4-substituted aminomethylpiperidine compounds, a method of preparation of the same, pharmaceutical compositions thereof, and a method of treating various physiological abnormalities therewith. Additional objects will become apparent hereinafter, and still others will be obvious to one skilled in the art to which this invention pertains.

SUMMARY OF THE INVENTION

What we believe to be our invention, then, comprises the following, inter alia, singly or in combination:

A 4-aminomethyl piperidine compound selected from those having formula 1:

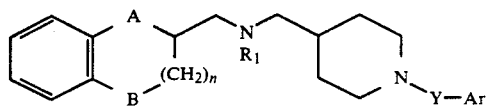

in which:

A and B, represent, independently of each other, oxygen, sulfur, or methylene;
n is 0 or 1;
$R_1$ represents hydrogen or $C_1$–$C_4$ alkyl;
Y represents carbonyl or methylene;
Ar represents phenyl, unsubstituted or substituted by one or more substituents selected from halogen, $C_1$–$C_4$ alkyl, $C_1$–$C_4$ alkoxy, and trifluoromethyl,
a pharmaceutically-acceptable salt thereof with an inorganic or organic acid and, when the compound contains an asymmetric carbon, a racemic mixture thereof, an enantiomer thereof, and mixtures of its enantiomers in all proportions; such a compound selected from the group consisting of:
1-(3-Methylbenzoyl) 4-(indan-2-yl methylaminomethyl) piperidine
1-(3-Methylbenzyl) 4-(indan-2-yl methylaminomethyl) piperidine
1-(3-Methylbenzoyl) 4-[(2,3-dihydro benzofuran-2-yl) methylaminomethyl] piperidine
1-(3-Methylbenzyl) 4-[(2,3-dihydro benzothiophen-2-yl)methylaminomethyl] piperidine
1-(3-Methylbenzoyl) 4-[(1,2,3,4-tetrahydro naphthalen-2-yl) methylaminomethyl] piperidine
1-(3-Methylbenzyl) 4-[(1,2,3,4-tetrahydro naphthalen-2-yl) methylaminomethyl] piperidine
1-(3-Methylbenzoyl) 4-[(3,4-dihydro 2[H].1-benzopyran-2-yl) methylaminomethyl] piperidine
1-(3-Methylbenzyl) 4-[(3,4-dihydro 2[H].1-benzopyran-2-yl) methylaminomethyl] piperidine
1-Benzoyl 4-(1,4-benzodioxan-2-yl methylaminomethyl) piperidine
1-Benzyl 4-(1,4-benzodioxan-2-yl methylaminomethyl) piperidine
1-(2-Methylbenzyl) 4-(1,4-benzodioxan-2-yl methylaminomethyl) piperidine
1-(3-Methylbenzoyl) 4-(1,4-benzodioxan-2-yl methylaminomethyl) piperidine
1-(3-Methylbenzyl) 4-(1,4-benzodioxan-2-yl methylaminomethyl) piperidine
1-(3-Methylbenzoyl) 4-[N-methyl N-(1,4-benzodioxan-2-yl methyl)aminomethyl] piperidine
1-(3-Methylbenzyl) 4-[N-methyl N-(1,4-benzodioxan-2-yl methyl)aminomethyl] piperidine
1-(4-Methylbenzoyl) 4-(1,4-benzodioxan-2-yl methylaminomethyl) piperidine
1-(4-Methylbenzyl) 4-(1,4-benzodioxan-2-yl methylaminomethyl) piperidine
1-(2-Fluorobenzoyl) 4-(1,4-benzodioxan-2-yl methylaminomethyl) piperidine
1-(2-Fluorobenzyl) 4-(1,4-benzodioxan-2-yl methylaminomethyl) piperidine
1-(3-Methoxybenzyl) 4-(1,4-benzodioxan-2-yl methylaminomethyl) piperidine
1-(3-Chlorobenzoyl) 4-(1,4-benzodioxan-2-yl methylaminomethyl) piperidine
1-(3-Chlorobenzyl) 4-(1,4-benzodioxan-2-yl methylaminomethyl) piperidine
1-(3-Trifluoromethylbenzoyl) 4-(1,4-benzodioxan-2-yl methylaminomethyl) piperidine
1-(3-Trifluoromethylbenzyl) 4-(1,4-benzodioxan-2-yl methylaminomethyl) piperidine
1-(3,4-Dimethoxybenzyl) 4-(1,4-benzodioxan-2-yl methylaminomethyl) piperidine
1-(3-Methylbenzoyl) 4-(1,3-benzodioxolan-2-yl methylaminomethyl) piperidine
1-(3,4-Dichlorobenzoyl) 4-(1,4-benzodioxan-2-yl methylaminomethyl) piperidine
1-(3-Methylbenzoyl) 4-(1,4-benzoxathian-2-yl methylaminomethyl) piperidine
1-(3-Methylbenzyl) 4-(1,4-benzoxathian-2-yl methylaminomethyl) piperidine
1-(3-Methylbenzyl) 4-(1,3-benzodioxolan-2-yl methylaminomethyl) piperidine
1-Benzoyl 4-[(3,4-dihydro-2[H].1-benzopyran-2-yl) methylaminomethyl] piperidine
1-Benzyl 4-[(3,4-dihydro-2[H].1-benzopyran-2-yl) methylaminomethyl] piperidine
1-(3-Chlorobenzoyl) 4-[(3,4-dihydro-2[H].1-benzopyran-2-yl) methylaminomethyl] piperidine
1-(3-Chlorobenzyl)4-[(3,4-dihydro-2[H].1-benzopyran-2-yl) methylaminomethyl] piperidine
1-(3-Methoxybenzoyl) 4-[(3,4-dihydro-2[H].1-benzopyran-2-yl) methylaminomethyl] piperidine
1-(3-Methoxybenzyl) 4-[(3,4-dihydro-2[H].1-benzopyran-2-yl) methylaminomethyl] piperidine
1-Benzoyl 4-(1,4-benzoxathian-2-yl methylaminomethyl) piperidine
1-Benzyl 4-(1,4-benzoxathian-2-yl methylaminomethyl) piperidine
1-(3-Chlorobenzoyl) 4-(1,4-benzoxathian-2-yl methylaminomethyl) piperidine
1-(3-Chlorobenzyl) 4-(1,4-benzoxathian-2-yl methylaminomethyl) piperidine
1-(3-Methoxybenzoyl) 4-(1,4-benzoxathian-2-yl methylaminomethyl) piperidine
1-(3-Methoxybenzyl) 4-(1,4-benzoxathian-2-yl methylaminomethyl) piperidine; and pharmaceutically-acceptable acid addition salts thereof.

Further, a pharmaceutical composition useful for the treatment of anxiety and depression and related serotoninergic system disorders which contains, as active principle, an amount of a compound as set forth in the foregoing which is effective for such purpose together with a pharmaceutically-acceptable diluent or carrier.

Moreover, a method of treating anxiety or depression or a related serotoninergic system disorder in a mammal afflicted therewith, comprising the step of administering to said mammal an amount of a compound as set forth in the foregoing which is effective for such purpose.

Also, a method of preparing a compound of formula 1 comprising the step of reacting an amine of formula 2 with a compound of formula 3

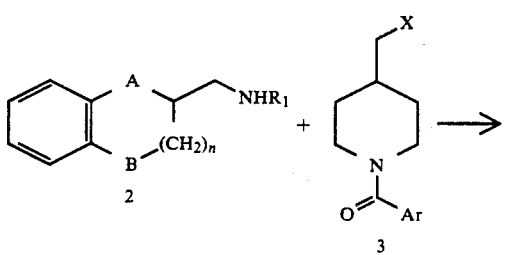

in which

A, B, n, $R_1$, and Ar are as defined in the foregoing, and

X represents a nucleofuge or leaving group, and wherein the compound of formula 4 corresponds to a compound of formula 1 wherein Y represents carbonyl.

Moreover, such a method wherein X is selected from methylsulfonyloxy, benzenesulfonyloxy, and p-toluenesulfonyloxy; and such a method wherein the reaction of an amine of formula 2 with a compound of formula 3 takes place in the absence or presence of a solvent; such a method wherein a solvent is present and selected from toluene, xylene, dimethylformamide, and acetonitrile; such a method wherein the temperature is between 50° and 160° C.; such a method when carried out in the presence of an organic base; such a method wherein the organic base is a tertiary amine; such a method when carried out in the presence of an inorganic base; such a method wherein the inorganic base is an alkali carbonate or hydrogen carbonate; such a method for preparing a compound of formula 1 in which Y represents a methylene radical, comprising the step of reducing a compound of general formula 4, prepared as set forth in the foregoing, in accord with the equation

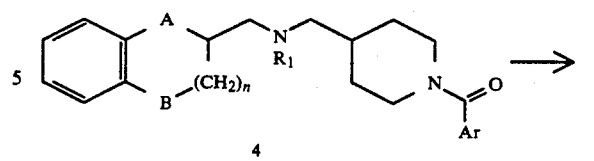

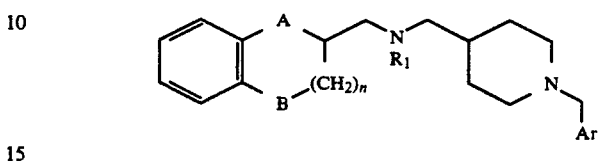

wherein A, B, n, $R_1$, and Ar are as above defined, by means of a hydride of boron or aluminum; such a method wherein the hydride is lithium aluminum hydride, aluminum hydride, a diborane/ether complex, or the diborane/methyl-sulfide complex, and the reduction is carried out in an inert solvent at a temperature between room temperature and the reflux temperature of the solvent; and also such a method wherein the solvent is ethyl ether or tetrahydrofuran.

GENERAL DESCRIPTION OF THE INVENTION

The compounds of the invention have general formula 1:

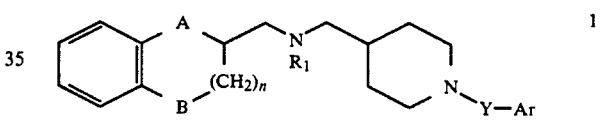

in which:

A and B, independently of each other, represent oxygen, sulfur, or methylene;

n can have the value of 0 or 1;

$R_1$ represents hydrogen or $C_1$–$C_4$ alkyl;

Y represents carbonyl or methylene;

Ar represents phenyl, substituted or not by one or more substituents selected from halogen, $C_1$–$C_4$ alkyl, $C_1$–$C_4$ alkoxy, and trifluoromethyl.

The invention also concerns salts of compounds of general formula 1 with pharmaceutically-acceptable inorganic or organic acids. By way of illustration but not of limitation, the acid used may be hydrochloric acid, fumaric acid, or maleic acid.

When the compounds of general formula 1 contain an asymmetrical carbon, the present invention concerns both the racemic mixtures and the different enantiomers and their admixtures in all proportions.

PREPARATION

The method of synthesis of the compounds of general formula 1 also forms a part of the present invention.

Synthesis of the Compounds of General Formula 1

Compounds of general formula 1 in which Y represents a carbonyl radical can be prepared by the reaction scheme:

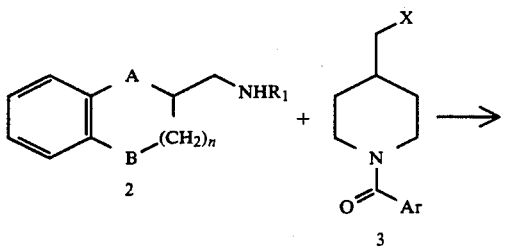

in which

A, B, n, $R_1$, and Ar are as defined above;

X represents a nucleofuge or leaving group such as methylsulfonyloxy, benzenesulfonyloxy, or p-toluenesulfonyloxy.

Starting amines 2 and piperidines of formula 3 are known and may be obtained by conventional methods.

The reaction between a compound of general formula 2 and a compound of general formula 3 takes place in either the absence or presence of a solvent, such as toluene, xylene, dimethylformamide, or acetonitrile, preferably at a temperature between 50° and 160° C. and preferably in the presence of an organic base such as a tertiary amine or of an inorganic base such as an alkali carbonate or hydrogen carbonate. In this way, a compound of general formula 4 is obtained which corresponds to general formula 1 when Y represents the carbonyl radical.

Compounds of general formula 1 in which Y represents a methylene radical can be prepared by the reaction scheme:

in which A, B, n, $R_1$, and Ar are as defined above.

The reduction of a compound of a compound of general formula 4, obtained as described above, is effected by means of a simple or complex hydride of boron or aluminum, for instance a double hydride of lithium and aluminum ($LiAlH_4$), aluminum hydride, a diborane/ether complex, or the diborane/methyl-sulfide complex, or any other equivalent reducing agent, within an inert solvent, such as ethyl ether or tetrahydrofuran. The reduction can be effected at room temperature or be accelerated by heating up to the reflux temperature of the solvent.

DETAILED DESCRIPTION OF THE INVENTION

The following examples are given to illustrate the invention, but are not to be construed as limiting. The elementary analyses and the IR and NMR spectra confirm the structure of the compounds obtained in accordance with the invention.

EXAMPLE 1

1-(3-methylbenzoyl) 4-(1,4-benzodioxan-2-yl methylaminomethyl) piperidine: Compound No. 12; A=0, B=0, n=1, $R_1$-H, Y=CO, Ar=3-Me.$C_6H_4$ A mixture of 7 g of 1-(3-methylbenzoyl) 4-(4-methyl-benzenesulfonyloxymethyl) piperidine and 3.2 g of 2-aminomethyl 1,4-benzodioxane is maintained at 150° C. with agitation for two hours. It is set aside to cool at room temperature, and chloroform and 10% ammonia are added to the vitreous mass. The chloroform phase is separated, washed with water, and dried over sodium sulfate. After filtration and evaporation of the solvent, the crude oil thus obtained is purified by silica-gel chromatography, using chloroform as eluent. 4 g of compound 12 are obtained, which are taken up in 50 ml of ethanol and treated with 1.21 g of maleic acid. Ethyl ether is added to the solution, thus obtaining 3.82 g of the maleate of compound 12 in the form of white crystals. MP: 138°-140° C.

EXAMPLE 2

1-(3-methylbenzyl) 4-(1.4-benzodioxan-2-yl methylaminomethyl) piperidine: Compound No. 13; A=0, B=0, n=1, $R_1$=H, Y=$CH_2$, Ar=3-Me.$C_6H_4$.

A solution of 2.8 g of 1-(3-methylbenzoyl) 4-(1,4-benzodioxan-2-yl methylaminomethyl) piperidine obtained by the method described in Example 1 in 15 ml of tetrahydrofuran is added drop by drop to a suspension of 0.29 g of $LiAlH_4$ and 10 ml of tetrahydrofuran, cooling by means of an ice bath. The temperature is allowed to rise to room temperature and, after 16 hours of agitation, the reaction mixture is hydrolyzed by addition of 2N caustic soda. It is filtered and the tetrahydrofuran evaporated under reduced pressure and the aqueous phase extracted by ethyl acetate. The extracts are washed with salt solution, dried over sodium sulfate, and filtered. The oil obtained upon evaporation of the solvent is purified by silica-gel chromatography using a 95:5 chloroform/methanol mixture as eluant. 1.1 g of compound 13 are obtained in the form of a pale yellow oil, which is then taken up in ethanol. An ethanolic solution of 0.69 g of maleic acid is added and, upon the addition of ethyl acetate, 1.0 g of dimaleate of compound 13 is obtained in the form of white crystals. MP: 195°-197° C.

Table 1 summarizes the main products synthesized, these illustrating the invention without, however, limiting the scope thereof.

TABLE 1

| Compound No. | A | B | n | $R_1$ | Y | Ar | salt | MP (°C.) |
|---|---|---|---|---|---|---|---|---|
| 1 | $CH_2$ | $CH_2$ | 0 | H | CO | 3-Me.$C_6H_4$ | Fumarate | 144–146 |
| 2 | $CH_2$ | $CH_2$ | 0 | H | $CH_2$ | 3-Me.$C_6H_4$ | Difumarate | 218–220 |

TABLE 1-continued

| Compound No. | A | B | n | $R_1$ | Y | Ar | salt | MP (°C.) |
|---|---|---|---|---|---|---|---|---|
| 3 | O | $CH_2$ | 0 | H | CO | $3\text{-Me.}C_6H_4$ | ½ Fumarate | 133–135 |
| 4 | S | $CH_2$ | 0 | H | $CH_2$ | $3\text{-Me.}C_6H_4$ | Difumarate | 211–213 |
| 5 | $CH_2$ | $CH_2$ | 1 | H | CO | $3\text{-Me.}C_6H_4$ | Maléate | 139–141 |
| 6 | $CH_2$ | $CH_2$ | 1 | H | $CH_2$ | $3\text{-Me.}C_6H_4$ | Difumarate | 208–210 |
| 7 | O | $CH_2$ | 1 | H | CO | $3\text{-Me.}C_6H_4$ | Fumarate | 141–143 |
| 8 | O | $CH_2$ | 1 | H | $CH_2$ | $3\text{-Me.}C_6H_4$ | Difumarate | 203–205 |
| 9 | O | O | 1 | H | CO | $C_6H_5$ | Fumarate | 164–166 |
| 10 | O | O | 1 | H | $CH_2$ | $C_6H_5$ | Difumarate | 198–200 |
| 11 | O | O | 1 | H | $CH_2$ | $2\text{-Me.}C_6H_4$ | Difumarate | 207–209 |
| 12 | O | O | 1 | H | CO | $3\text{-Me.}C_6H_4$ | Maléate | 138–140 |
| 13 | O | O | 1 | H | $CH_2$ | $3\text{-Me.}C_6H_4$ | Dimaléate | 195–197 |
| 14 | O | O | 1 | Me | CO | $3\text{-Me.}C_6H_4$ | Fumarate | 138–140 |
| 15 | O | O | 1 | Me | $CH_2$ | $3\text{-Me.}C_6H_4$ | Difumarate | 151–153 |
| 16 | O | O | 1 | H | CO | $4\text{-Me.}C_6H_4$ | Fumarate | 129–131 |
| 17 | O | O | 1 | H | $CH_2$ | $4\text{-Me.}C_6H_4$ | Difumarate | 178–180 |
| 18 | O | O | 1 | H | CO | $2\text{-F.}C_6H_4$ | Fumarate | 128–130 |
| 19 | O | O | 1 | H | $CH_2$ | $2\text{-F.}C_6H_4$ | Difumarate | 189–191 |
| 20 | O | O | 1 | H | $CH_2$ | $3\text{-MeO.}C_6H_4$ | Difumarate | 203–205 |
| 21 | O | O | 1 | H | CO | $3\text{-Cl.}C_6H_4$ | Fumarate | 140–142 |
| 22 | O | O | 1 | H | $CH_2$ | $3\text{-Cl.}C_6H_4$ | Difumarate | 169–171 |
| 23 | O | O | 1 | H | CO | $3\text{-CF}_3\text{.}C_6H_4$ | Fumarate | 138–140 |
| 24 | O | O | 1 | H | $CH_2$ | $3\text{-CF}_3\text{.}C_6H_4$ | Difumarate | 214–216 |
| 25 | O | O | 1 | H | $CH_2$ | $3,4\text{-}(MeO)_2\text{.}C_6H_3$ | Difumar. | 204–206 |
| 26 | O | O | 0 | H | CO | $3\text{-Me.}C_6H_4$ | Fumarate | 137–139 |
| 27 | O | O | 1 | H | CO | $3,4\text{-Cl}_2\text{.}C_6H_3$ | Fumarate | 172–174 |
| 28 | O | S | 1 | H | CO | $3\text{-Me.}C_6H_4$ | Maléate | 114–116 |
| 29 | O | S | 1 | H | $CH_2$ | $3\text{-Me.}C_6H_4$ | Difumarate | 208–210 |
| 30 | O | O | 0 | H | $CH_2$ | $3\text{-Me.}C_6H_4$ | Difumarate | 195–197 |
| 31 | O | $CH_2$ | 1 | H | CO | $C_6H_5$ | Maléate | 151–153 |
| 32 | O | $CH_2$ | 1 | H | $CH_2$ | $C_6H_5$ | Dimaléate | 189–191 |
| 33 | O | $CH_2$ | 1 | H | CO | $3\text{-Cl.}C_6H_4$ | Maléate | 179–181 |
| 34 | O | $CH_2$ | 1 | H | $CH_2$ | $3\text{-Cl.}C_6H_4$ | Dimaléate | 190–192 |
| 35 | O | $CH_2$ | 1 | H | CO | $3\text{-MeO.}C_6H_4$ | ½ Fumarate | 142–144 |
| 36 | O | $CH_2$ | 1 | H | $CH_2$ | $3\text{-MeO.}C_6H_4$ | Dimaléate | 196–198 |
| 37 | O | S | 1 | H | CO | $C_6H_5$ | Maléate | 147–149 |
| 38 | O | S | 1 | H | $CH_2$ | $C_6H_5$ | Difumarate | 206–208 |
| 39 | O | S | 1 | H | CO | $3\text{-Cl.}C_6H_4$ | Maléate | 127–129 |
| 40 | O | S | 1 | H | $CH_2$ | $3\text{-Cl.}C_6H_4$ | Difumarate | 196–198 |
| 41 | O | S | 1 | H | CO | $3\text{-MeO.}C_6H_4$ | Maléate | 108–110 |
| 42 | O | S | 1 | H | $CH_2$ | $3\text{-MeO.}C_6H_4$ | Dimaléate | 199–201 |

As is clear from the foregoing, the compounds of the present invention contain a salt-forming group and can therefore be administered to man or animal orally or parenterally either in the form of the free base or in the form of a therapeutically-acceptable salt. The new derivatives which are bases can be converted into acid addition salts with acids, which acid addition salts form part of the invention. These acid addition salts can be obtained by reaction of the new basic derivatives with an acid in a suitable solvent, such as for example, in the mineral acid series, hydrochloric, hydrobromic, methanesulphonic, sulphuric, and phosphoric and, in the organic series, acetic, propionic, maleic, fumaric, tartaric, citric, oxalic, and benzoic acid, to name only a few. The selection of the free base or acid addition salt thereof in preparation of the desired acid addition salt in any particular case will be apparent and fully within the capability of one skilled in the art. Such novel compounds of the invention are frequently used in the form of their pharmaceutically-acceptable acid addition salts, such as the hydrochlorides, hydrobromides, or the like, since the salt form is usually the best form for pharmaceutical formulations. Innumerable other pharmaceutically-acceptable acid addition salts can be prepared from the hydrochlorides or other acid addition salts via the free bases in conventional manner.

EXPERIMENTAL

Various toxicological and pharmacological tests were carried out on the compounds forming the object of the invention, which evidenced their suitability as substances having a valuable therapeutic activity.

Affinity for Serotoninergic 5-HT$_{1A}$ Receptors

Thus, they have been made the object of a study concerning their affinity for serotoninergic receptors of type 5-HT$_{1A}$. The 5-HT$_{1A}$ binding studies were carried out in accordance with Peroutka's technique (see: Peroutka, S. J.: J. Neurochem. 47:529–540, 1986). Male Charles River rats are stunned and decapitated, the brain is removed and dissected. The different cerebral areas obtained are used or preserved at minus 20° C. The hippocampus is crushed with Polytron ® (20 seconds at 7) in 20 volumes of 50 mM Tris-HCl buffer (pH 7.7 at 25° C.) and centrifuged at 45,000 g for 10 min. The residue is separated, taken up in the same volume of Tris buffer and incubated for 10 min at 37° C., and then again centrifuged for 10 min at 45, 000 g. The residue is then taken up in 100 volumes of Tris-HCl buffer containing 10 μm of Pargyline, 4 mM CaCl$_2$ and 0.1% ascorbic acid. The mixture obtained is Dounce homogenized.

The binding is effected starting with 0.8 ml of the above membrane suspension to which 0.1 ml of $^3$H-8-OH-DPAT ligand is added (in a concentration of 1 nM) and either 0.1 ml of Tris buffer (control) or the compound of the present invention is added. After incubation for 30 min at 25° C., the mixture is filtered on GF/B (Whatman) and rinsed with 5 ml of iced Tris-HCl buffer. The residue and the filter are finally introduced into a vial containing 3 ml of Instage ® scintillating liquid (Packard) and the radioactivity is measured with a Packard counter (Tri-Carbs ®). The IC$_{50}$ are determined graphically for a ligand concentration of 1 nM. Table 2 shows, by way of example, the IC$_{50}$ for the 5-HT$_{1A}$ receptors for certain representative derivatives of the invention.

TABLE 2

| Compound No. | IC$_{50}$ nM |
|---|---|
| 3 | 7.5 |
| 5 | 12.5 |
| 7 | 3.8 |
| 9 | 3.0 |
| 17 | 4.4 |
| 22 | 2.1 |
| Buspirone | 23 |

The results of the tests show that the compounds of general formula 1 possess high affinity for the serotoninergic receptors of type 5-HT$_{1A}$, being considerably more active in this regard than the reference standard Buspirone.

Therapeutic Applications

Based on their pharmacological properties, the compounds of the invention may be used in human therapeutics for treatment of related serotoninergic system disorders, such as are involved in anxiety, depression, and disturbance of sleep, as well as in vascular, cardiovascular, and cerebrovascular disorders such as hypertension or migraine, and for the regulation of the intake of food, these being applications which are reasonably indicated for compounds having such a high degree of affinity for serotoninergic receptors of type 5-HT$_{1A}$.

Pharmaceutical Compositions and Method-of-Treating

Pharmaceutical compositions containing the active compounds or principles of the present invention may be prepared in a form for oral, rectal, parenteral, topical, or other administration, for example, in the form of pills, capsules, gels, or solutions containing the active ingredient and one or more appropriate excipients, carriers, or diluents. It is likewise possible to associate a compound of the present invention in such a pharmaceutical composition with one or more other active principles which are therapeutically-active and pharmaceutically-acceptable.

A pharmaceutical composition of the invention may accordingly be defined as a pharmaceutical composition, useful for the treatment of an ailment which requires treatment with a compound having affinity for serotoninergic receptors of type 5-HT$_{1A}$, and especially such ailments as anxiety, depression, disturbance of sleep, or for the regulation of the intake of food, or for the treatment of vascular, cardiovascular, and cerebrovascular disorders such as hypertension or migraine, which contains, as active principle, an amount of one or more compounds of the present invention which is effective for such purpose.

A method of treating according to the present invention may accordingly be defined as a method of treating an ailment which requires for its treatment a compound having an affinity for serotoninergic receptors of type 5-HT$_{1A}$, and especially anxiety, depression, and disturbance of sleep, or for the regulation of the intake of food, or for the treatment of vascular, cardiovascular, and cerebrovascular disorders such as hypertension or migraine, in a mammal afflicted therewith, comprising the step of administering to said mammal an amount of a compound of the invention which is effective for such purpose, preferably in the form of a pharmaceutical composition thereof in which it is present together with a pharmaceutically-acceptable diluent or carrier.

It will of course be apparent to one skilled in the art that the amount of the active ingredient must be an effective anxiolytic, antidepressive, or other effective amount and also that the ailment or condition treated must be one which is susceptible to treatment with a compound of the invention, that is, one which is responsive to treatment therewith.

A pharmaceutical composition of the invention may, for example, contain between about 10 and about 200 mg of active ingredient per unit dosage form. It will, however, be apparent to one skilled in the art that the exact dosage and dosage form, as well as the particular pharmaceutically-acceptable diluent, carrier, or adjuvant employed, as well as the particular type of pharmaceutical form employed, whether tablet, capsule, suppository, emulsion, dispersion, or injectable solution, will be dependent upon the exact condition involved, as well as the condition of the patient involved, and as usual in accord with the preferences and directions of the physician or veterinarian in charge.

It is therefore seen from the foregoing that new compounds, pharmaceutical compositions thereof, a method of treating and ameliorating susceptible ailments or conditions with such a compound or pharmaceutical composition of the invention, and a method of making the same, have all been provided, and that all of the objects of the invention have thus been fulfilled.

It is to be understood that the present invention is not to be limited to the exact compounds, compositions, procedures, or formulations disclosed, as numerous modifications and changes therein will immediately become apparent to one skilled in the art to which this invention pertains, wherefore the present invention is to be understood as limited only by the full scope which can be legally accorded to the appended claims.

We claim:

1. A 4-aminomethyl piperidine compound selected from those having formula 1:

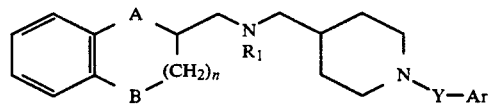

in which

A and B, represent, independently of each other, oxygen, sulfur, or methylene;

n is 0 or 1;

R$_1$ represents hydrogen or C$_1$-C$_4$ alkyl;

Y represents carbonyl or methylene;

Ar represents phenyl, unsubstituted or substituted by a substituent selected from halogen, C$_1$-C$_4$ alkyl, C$_1$-C$_4$ alkoxy, and trifluoromethyl, a pharmaceutically-acceptable salt thereof with an inorganic or organic acid and, when the compound contains an asymmetric carbon an enantiomer thereof.

2. A compound of claim 1, selected from the group consisting of:

1-(3-Methylbenzoyl) 4-(indan-2-yl methylaminomethyl) piperidine 1-(3-Methylbenzyl) 4-(indan-2-yl methylaminomethyl) piperidine 1-(3-Methylbenzoyl) 4-[(2,3-dihydro benzofuran-2-yl) methylaminomethyl] piperidine
1-(3-Methylbenzyl) 4-[(2,3-dihydro benzothiophen-2yl)methylaminomethyl] piperidine
1-(3-Methylbenzoyl) 4-[(1,2,3,4-tetrahydro naphthalen-2-yl) methylaminomethyl] piperidine
1-(3-Methylbenzyl) 4-[(1,2,3,4-tetrahydro naphthalen-2-yl) methylaminomethyl] piperidine
1-(3-Methylbenzoyl) 4-[(3,4-dihydro 2[H].1-benzopyran-2-yl) methylaminomethyl] piperidine
1-(3-Methylbenzyl) 4-[(3,4-dihydro 2[H].1-benzopyran-2-yl) methylaminomethyl] piperidine
1-Benzoyl 4-(1,4-benzodioxan-2-yl methylaminomethyl) piperidine
1-Benzyl 4-(1,4-benzodioxan-2-yl methylaminomethyl) piperidine
1-(2-Methylbenzyl) 4-(1,4-benzodioxan-2-yl methylaminomethyl) piperidine
1-(3-Methylbenzoyl) 4-(1,4-benzodioxan-2-yl methylaminomethyl) piperidine
1-(3-Methylbenzyl) 4-(1,4-benzodioxan-2-yl methylaminomethyl) piperidine
1-(3-Methylbenzoyl) 4-[N-methyl N-(1,4-benzodioxan-2-yl methyl)aminomethyl] piperidine
1-(3-Methylbenzyl) 4-[N-methyl N-(1,4-benzodioxan-2-yl methyl)aminomethyl] piperidine
1-(4-Methylbenzoyl) 4-(1,4-benzodioxan-2-yl methylaminomethyl) piperidine
1-(4-Methylbenzyl) 4-(1,4-benzodioxan-2-yl methylaminomethyl) piperidine
1-(2-Fluorobenzoyl) 4-(1,4-benzodioxan-2-yl methylaminomethyl) piperidine
1-(2-Fluorobenzyl) 4-(1,4-benzodioxan-2-yl methylaminomethyl) piperidine
1-(3-Methoxybenzyl) 4-(1,4-benzodioxan-2-yl methylaminomethyl) piperidine
1-(3-Chlorobenzoyl) 4-(1,4-benzodioxan-2-yl methylaminomethyl) piperidine
1-(3-Chlorobenzyl) 4-(1,4-benzodioxan-2-yl methylaminomethyl) piperidine
1-(3-Trifluoromethylbenzoyl) 4-(1,4-benzodioxan-2-yl methylaminomethyl) piperidine
1-(3-Trifluoromethylbenzyl) 4-(1,4-benzodioxan-2-yl methylaminomethyl) piperidine
1-(3,4-Dimethoxybenzyl) 4-(1,4-benzodioxan-2-yl methylaminomethyl) piperidine
1-(3-Methylbenzoyl) 4-(1,3-benzodioxolan-2-yl methylaminomethyl) piperidine
1-(3,4-Dichlorobenzoyl) 4-(1,4-benzodioxan-2-yl methylaminomethyl) piperidine
1-(3-Methylbenzoyl) 4-(1,4-benzoxathian-2-yl methylaminomethyl) piperidine
1-(3-Methylbenzyl) 4-(1,4-benzoxathian-2-yl methylaminomethyl) piperidine
1-(3-Methylbenzyl) 4-(1,3-benzodioxolan-2-yl methylaminomethyl) piperidine
1-Benzoyl 4-[(3,4-dihydro-2[H].1-benzopyran-2-yl) methylaminomethyl] piperidine
1-Benzyl 4-[(3,4-dihydro-2[H].1-benzopyran-2-yl) methylaminomethyl] piperidine
1-(3-Chlorobenzoyl) 4-[(3,4-dihydro-2[H].1-benzopyran-2-yl) methylaminomethyl] piperidine
1-(3-Chlorobenzyl) 4-[(3,4-dihydro-2[H].1-benzopyran-2-yl) methylaminomethyl] piperidine
1-(3-Methoxybenzoyl) 4-[(3,4-dihydro-2[H].1-benzopyran-2-yl) methylaminomethyl] piperidine
1-(3-Methoxybenzyl) 4-[(3,4-dihydro-2[H].1-benzopyran-2-yl) methylaminomethyl] piperidine
1-Benzoyl 4-(1,4-benzoxathian-2-yl methylaminomethyl) piperidine
1-Benzyl 4-(1,4-benzoxathian-2-yl methylaminomethyl) piperidine
1-(3-Chlorobenzoyl) 4-(1,4-benzoxathian-2-yl methylaminomethyl) piperidine
1-(3-Chlorobenzyl) 4-(1,4-benzoxathian-2-yl methylaminomethyl) piperidine
1-(3-Methoxybenzoyl) 4-(1,4-benzoxathian-2-yl methylaminomethyl) piperidine
1-(3-Methoxybenzyl) 4-(1,4-benzoxathian-2-yl methylaminomethyl) piperidine and pharmaceutically-acceptable acid addition salts thereof.

3. A pharmaceutical composition useful for the treatment of anxiety and depression which contains, as active principle, an amount of a compound of claim 1 which is effective for such purpose together with a pharmaceutically-acceptable diluent or carrier.

4. A pharmaceutical composition useful for the treatment of anxiety and depression which contains, as active principle, an amount of a compound of claim 2 which is effective for such purpose together with a pharmaceutically-acceptable diluent or carrier.

5. A method of treating anxiety or depression in a mammal afflicted therewith, comprising the step of administering to said mammal an amount of a compound of claim 1 which is effective for such purpose.

6. A method of treating anxiety or depression in a mammal afflicted therewith, comprising the step of administering to said mammal an amount of a compound of claim 2 which is effective for such purpose.

* * * * *

UNITED STATES PATENT AND TRADEMARK OFFICE
CERTIFICATE OF CORRECTION

PATENT NO. : 5,286,735
DATED : February 15, 1994
INVENTOR(S) : Bernard Bounnaud and Dennis Bigg It is certified that error appears in the above-indentified patent and that said Letters Patent is hereby corrected as shown below:

Col. 4, line 43; "$C_1$--$C_4$" should read -- $C_1$-$C_4$ --.
Col. 5, line 56; "The reduction of a compound of a compound of" should read -- The reduction of a compound of --.
Col. 6, line 35; "4-(1.4-benzodioxan-2-yl" should read
    -- 4-(1,4-benzodioxan-2-yl --.
Table 1, Compound No. 10; The listing under the "Ar" column should read -- $C_6H_5$ --.
Col. 8, line 56; delete the space between "45," and "000".
Col. 8, line 68; "Instage" should read -- Instagel --.
Col. 10, line 62; insert a comma after "carbon".
Col. 11, line 4; "2yl" should read -- 2-yl --.

Signed and Sealed this

Thirteenth Day of September, 1994

Attest:

BRUCE LEHMAN

Attesting Officer          Commissioner of Patents and Trademarks